(12) United States Patent
Wang et al.

(10) Patent No.: US 12,313,513 B2
(45) Date of Patent: May 27, 2025

(54) RANDOM PARTICLE GENERATION METHOD BASED ON PARTICLE SIZE DISTRIBUTION

(71) Applicant: Dalian University of Technology, Dalian (CN)

(72) Inventors: Dayong Wang, Dalian (CN); Liang Zhao, Dalian (CN); Qilin Wang, Dalian (CN); Mengxin Li, Dalian (CN); Wei Wei, Dalian (CN)

(73) Assignee: Dalian University of Technology, Dalian (CN)

( * ) Notice: Subject to any disclaimer, the term of this patent is extended or adjusted under 35 U.S.C. 154(b) by 367 days.

(21) Appl. No.: 17/960,016

(22) Filed: Oct. 4, 2022

(65) Prior Publication Data

US 2023/0251178 A1  Aug. 10, 2023

(30) Foreign Application Priority Data

Feb. 10, 2022 (CN) .......................... 202210127331.6

(51) Int. Cl.
*G01N 15/02* (2024.01)
*G16C 20/40* (2019.01)

(52) U.S. Cl.
CPC ............ *G01N 15/02* (2013.01); *G16C 20/40* (2019.02); *G01N 2015/0294* (2013.01)

(58) Field of Classification Search
CPC . G01N 15/02; G01N 2015/0294; G16C 20/40
See application file for complete search history.

(56) References Cited

U.S. PATENT DOCUMENTS

| 2012/0111117 | A1* | 5/2012 | Prakash | ............ G01N 29/4472 |
| | | | | 73/599 |
| 2018/0144540 | A1* | 5/2018 | Novak | ..................... G06T 15/08 |
| 2018/0188148 | A1* | 7/2018 | Trainer | ............. G01N 15/0227 |

FOREIGN PATENT DOCUMENTS

| CN | 107680131 A | * | 2/2018 | ............. G06T 17/00 |
| CN | 112668254 A | * | 4/2021 | |
| WO | WO-2011110755 A2 | * | 9/2011 | ........... G06F 19/704 |

* cited by examiner

*Primary Examiner* — Lisa M Caputo
*Assistant Examiner* — Nyla Gavia
(74) *Attorney, Agent, or Firm* — Mahamedi IP Law LLP

(57) ABSTRACT

The present disclosure provides a random particle generation method based on particle size distribution, which can accord with the particle size distribution characteristics of a geological structure. According to this method, random particle generation is adopted, so that a common spherical structure is avoided, and a generated particle structure is very similar to a real soil structure. Based on actual particle size distribution, particles with different particle sizes are generated by batch generation, particle seeds are generated at random pore locations, and particles are generated based on the seeds. By providing a random particle generation method based on particle size distribution, a soil structure in a form of porous media can be restored by means of simulation, which thus provides a porous medium model for the research of groundwater infiltration and fossil energy exploitation.

8 Claims, 4 Drawing Sheets

RANDOM PARTICLE GENERATION METHOD BASED ON PARTICLE SIZE DISTRIBUTION

CROSS REFERENCE TO RELATED APPLICATION

This patent application claims the benefit and priority of Chinese Patent Application No. 202210127331.6, filed with the China National Intellectual Property Administration on Feb. 10, 2022, the aforementioned application being incorporated by reference herein in its entirety as part of the present application.

TECHNICAL FIELD

The present disclosure relates to a method for constructing a three-dimensional porous medium, and in particular to a random particle generation method based on particle size distribution.

BACKGROUND

The geological structure in a form of porous media is commonly found in the study of groundwater seepage, oil exploitation, natural gas exploitation, hydrate exploitation and so on. The transmission characteristics on a macroscale depend on the characteristics of the geological structure on a microscale. Therefore, obtaining a more realistic in situ soil structure is beneficial to improve the accuracy of the research results.

At present, available methods include field mining, experimental preparation and numerical simulation. Among them, field mining is costly, difficult to implement, and time-consuming; experimental preparation takes a long time, and cannot achieve process analysis; and these two methods, when reconstructing a three-dimensional structure by CT scanning, may have problems such as difficulty in interface tracking, and lagging. In view of this, many researchers have begun to construct structures in the form of porous media by numerical simulation. At present, researchers have proposed a variety of structural models, such as stochastic model, connecting rod model, particle chain model, capillary model, statistical model, network model, fractal model and so on. Wang et al. (WANG M, PAN N. Numerical analyses of effective dielectric constant of multiphase microporous media [J]. Journal of Applied Physics, 2007, 101 (11):114102-1-114102-8.) proposed a quartet structure generation set (QSGS) algorithm to generate porous media based on random cluster growth theory. The foregoing method can generate porous media which have various shapes and are intuitively similar to the structure of real soil. At present, it has been widely used by many researchers for the simulation of geological structure (Zhong Siwei, Quantitative study on microscopic pore structure of soil reconstructed by quartet structure generation set, Wuhan University of Technology, 2018). Although this method can achieve a structure similar to that of real soil, the particle distribution is relatively uniform. Nevertheless, during geological exploration, particle size distribution of soil is one of key data parameters in geological analysis. Thus it can be seen that this method has certain defects.

SUMMARY

To solve the problem in the prior art, the present disclosure provides a random particle generation method based on particle size distribution. By adoption of the method, a soil structure that meet the geological characteristics can be generated according to particle size distribution of soil, and the clustering-based generation mode can help to generate a structure of porous media which is more similar to the real soil.

The present disclosure adopts the following technical solution: a random particle generation method based on particle size distribution, including:

step 1, obtaining geological structure-related information, and determining a simulation target, where the geological structure-related information includes particle size distribution-related information and porosity of target soil;

step 2, determining initial parameters of a simulation system, including a size of a three-dimensional region of the simulation system, porosity of a simulation system, particle size distribution-related information of the simulation system, and a growth probability of a solid-phase point of the simulation system in each direction; where the porosity of the simulation system refers to the porosity of the target soil in step 1, and the particle size distribution-related information of the simulation system refers to the particle size distribution-related information of the target soil, and is indicative of a correspondence between a particle size and a distribution probability of a particle;

step 3, determining, according to the initial parameters in step 2, an estimated value in a simulation process, where step 3 specifically includes:

step 3.1, setting: total number of solid-phase points of the simulation system=total number of grids in a simulation region×(1−porosity);

step 3.2, setting: total number N of solid-phase points of particles with a same particle size=distribution probability corresponding to each particle size×total number of grids in the system;

step 3.3, setting: upper bound of solid-phase points of an individual particle $n=\pi D^3/6$, where D denotes a particle diameter; and the upper bound of the solid-phase points is calculated according to the volume of a sphere; and step 3.4, setting: number of random seeds with a particle size of D=total number of particles with a particle size of D (=N/n), where N/n is rounded up to an integer to meet the requirement for the total number of solid-phase points; and step 4, constructing porous media by generating particles in batches in a descending order of particle sizes, where step 4 specifically includes:

step 4.1, constructing a first batch of particles with a particular particle size: generating and numbering seeds of N/n particles, and growing subsequent particles based on the seeds, where the growth of the particle matches the growth probability of the solid-phase point in each direction in step 2, and the generated solid-phase point is numbered in the same way as the seed so as to determine the volume change of the particles; by traversing the solid-phase point for growth, determining whether the particle grows to the upper bound n of solid-phase points for an individual particle, and if so, stopping growth of the particle; and if the total number N of solid-phase points of the particle with the particle size is reached in the traversal process, finishing constructing the batch of particles with the particle size;

step 4.2, generating a subsequent batch of particles, where some solid-phase points already exist in the simulation region, so in the process of generating a second batch of particles and a subsequent batch of particles with a particular particle size, it is necessary to calculate the minimum distance between all the pore points and the solid-phase point; and after the previous batch of particles are generated, calculating a minimum distance I of each of pore points from the solid-phase point, randomly generating a latter batch of seeds on the pore points meeting the condition I≥½D, and then carrying out the same construction step as step 4.1 until the number of solid-phased points required for the batch of particles is reached, where D represents a particle size of the present batch of particles; and step 4.3, repeating step 4.2 to generate subsequent particles, and when a last batch of particles with a particular particle size are generated, determining whether the total number of solid-phase points in the system reaches the total number of solid-phase points in the simulation system in step 3.1, and if so, finishing the generation step.

Further, in step 1, the particle size distribution-related information of the target soil is determined by dividing the range of a particle size into n segments with each segment containing multiple data points, taking a weighted average of the particle sizes of the data points with respect to the distribution probability within each segment of range as a particle size of the segment, and taking a sum of the distribution probability of the data points within each segment of range as a distribution probability of the segment.

Further, in step 1, the simulation method requires the computer to have a certain processing power. Therefore, when the value of n is too large, the calculation time then becomes too long, so in order to take into account both the calculation time and the simulation accuracy, n is ranging from 2 to 7.

Further, the growth probability of the solid-phase point of the simulation system in each direction as determined in step 2 refers to the probability that a central solid-phase point achieves solid-phase growth in each direction; and there are 26 growth directions for the solid-phase point, including 6 face-centered directions, 12 edge-centered directions and 8 corner-point directions, totally three major directions.

Further, in step 2, if the particles have isotropic structures, a growth probability in each of the major directions is the same.

Further, in step 2, a growth probability P1 in each of the 6 face-centered directions is 0.001-0.0001, a growth probability P2 in each of the 12 edge-centered directions meets $P2=P^{1/4}$, and a growth probability P3 in each of the 8 corner-point directions meets $P3=P^{1/16}$.

Further, in step 2, the three-dimensional region of the simulation system is a square structure.

Further, in step 1, the particle size distribution-related information of target soil can be obtained from the Geological Survey, papers, experiments, etc.

Further, in step 1, the particle size distribution should be divided into as few segments as possible, which can improve the generation efficiency, and especially avoid direct use of a particle size distribution function.

The present disclosure has the following beneficial effects: a porous medium generation method based on particle size distribution is constructed, which can accord with the particle size distribution characteristics of a geological structure. According to this method, random particle generation is adopted, so that a common spherical structure is avoided, and a generated particle structure is very similar to a real soil structure. Therefore, by providing a random particle generation method based on particle size distribution, a soil structure in a form of porous media can be restored by means of simulation, which thus provides a porous medium model for the research of groundwater infiltration and fossil energy exploitation.

DETAILED DESCRIPTION OF THE EMBODIMENTS

The technical solution of the present disclosure will be described in detail hereinafter with reference to the accompanying drawings.

Figure 1:
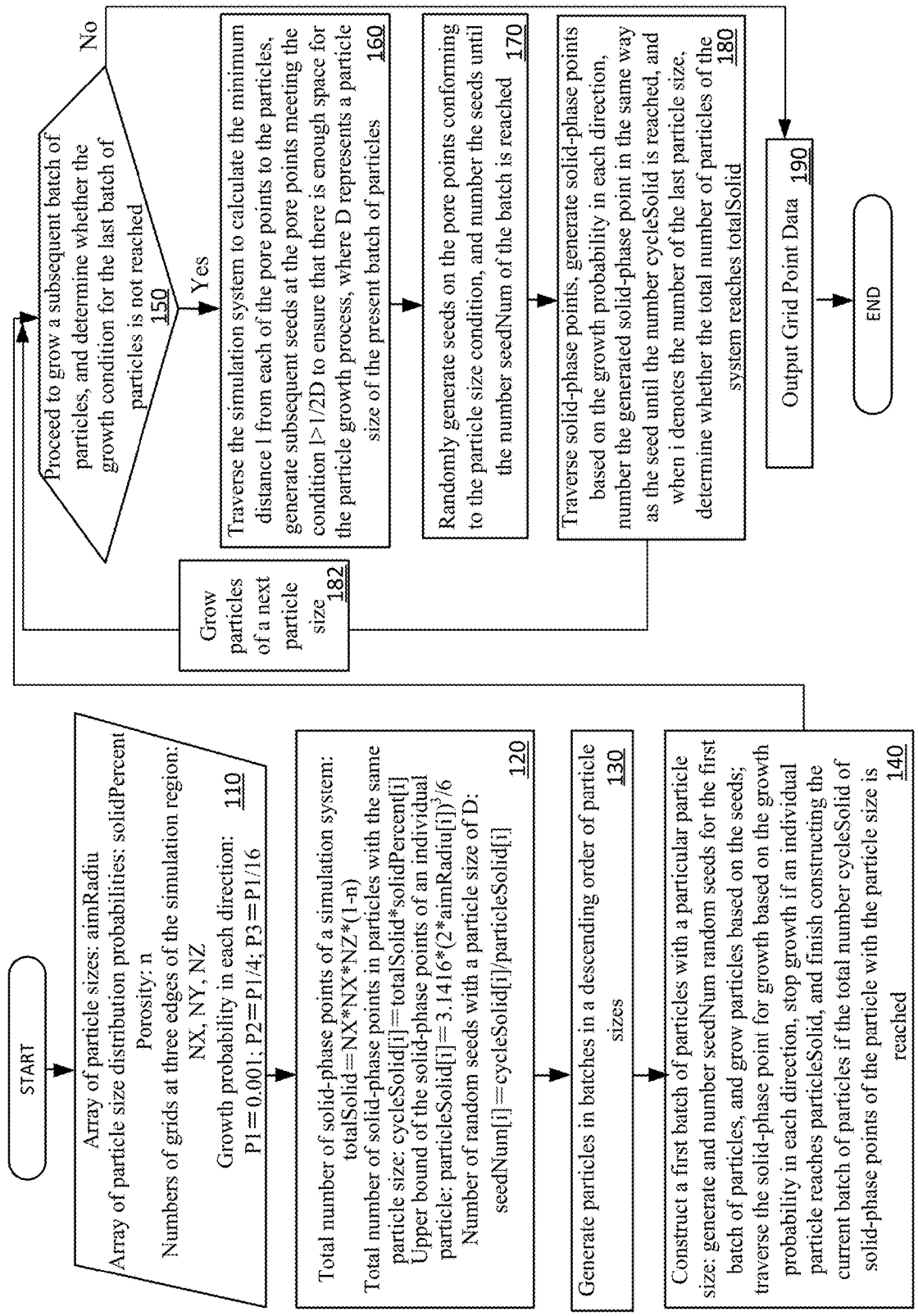
FIG. 1 is a flowchart of a calculation process according to the present disclosure.

The present disclosure is described in detail below with reference to the accompanying drawings and specific embodiments. The specific embodiment of the method according to the present disclosure is shown in the flow chart of FIG. 1, which shows illustrative steps (110-190) in accordance with one or more embodiments.

Figure 2:
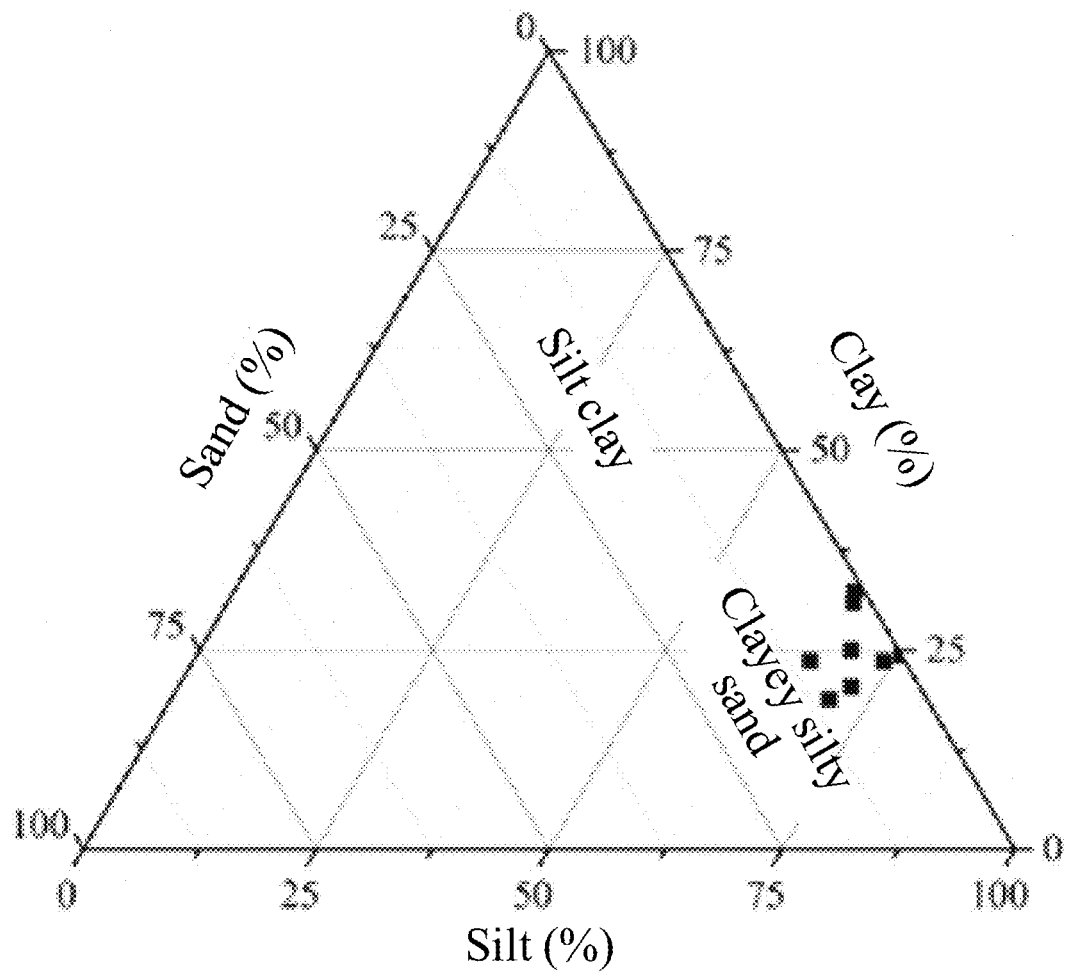
FIG. 2 is a map depicting geological information of South China Sea referenced by an embodiment of the present disclosure.

In at least some embodiments, a method is adopted to simulate the geological structure of clayey silty sand in a hydrate reservoir of Shenhu Area located in the South China Sea, as well as the isotropy of the geological structure. In more detail:

Step 1, acquire geological structure-related information: simulate the isotropy of the geological structure, and according to the particle size distribution characteristics shown in FIG. 2, distribution ratios of clay particle size (<4 um), silt particle size (4-63 um) and sand particle size (>63 um) are 18.76%-32.29%, 66.21%-75.02%, and 0.06%-10.56%, respectively. The average particle size is 12 um, and the porosity is 33%. Therefore, during the simulation process, the particle size distributions are set to be 4 (26%), 12 (70%) and 64 (4%), which not only meets the distribution range, but also accords with the average particle size.

Step 2, acquire initial data: the simulation region has grids with a total size of 100*100*100, and the edge length of a single grid is 2 um, so in the simulation process, according to the descending order of particle radius, and with the grid as a unit, the array of particle sizes is aimRadiu[3]={16,3,1}, and the array of particle size distribution probabilities is solidPercent[3]={0.04,0.70,0.26}. The porosity n is 0.33, and regarding the numbers of grids at three edges of the simulation region, NX=NY=NZ=100. The growth probability in each direction is as follows: a growth probability P1 in each face-centered directions is P1=0.001, a growth probability P2 in each edge-centered direction is P2=¼, and a growth probability P3 in each corner-point direction is P3=1/16.

Step 3, calculate an estimated value in the simulation process according to initial parameters: calculate, according to the size and porosity of the simulation region, the total number of solid-phase points of the simulation system as follows: totalSolid=NX*NX*NZ*(1−n), namely totalSolid=100*100*100*(1−0.33)=670000. Conduct calculation based on particle size distribution-related information, and the results are as follows: for a particle with a particle radius of 16, the number of solid-phase points in an individual particle is 17,158, the total number of solid-phase points after rounding operation is 26,800, and the number of particle seeds generated is equal to the number of particles (=2); for a particle with a particle radius of 3, the number of solid-phase points in an individual particle is 114, the total number of solid-phase points is 469,000, and the number of particle seeds is 4,115; and for a particle with a particle radius of 5, the number of solid-phase points in an individual particle is 5, the total number of solid-phase points is 174,200, and the number of particle seeds is 34,840. (the decimal values are all rounded up to ensure that the total number of solid-phase points can meet the requirements for the total number of solid-phase points with the same particle size). According to a descending order, the total number of solid-phase points in particles with the same particle size is:
cycleSolid[i]=totalSolid*solidPercent[i], that is, cycleSolid[3]={26800,469000,174200}; the upper bound of the solid-phase points of an individual particle is: particleSolid[i]=3.1416*(2*aimRadiu[i])$^3$/6, that is, particleSolid[3]={17158,114,5}; and the number of random seeds with a particle size of D is: seedNum[i]=cycleSolid[i]/particleSolid[i], that is, seedNum[3]={2,4115,34840}.

Step 4, conduct iterative operation: since there are three kinds of particle sizes, the growth of the first batch of particles is performed according to the procedure, the particle radius is 16, and the random growth begins after 2 seeds are randomly generated, and the total number of solid-phase points in each particle cannot exceed the target volume of the particles. After the total number of solid-phase points reaches 26,800, finish generation of the batch of particles, and proceed to generate the subsequent batch of particles. As the second batch of particles start to be generated, it is necessary to determine the distance between the remaining pores and a solid-phase point, then randomly generate seeds at a position that meets the conditions, and then go through the same process as the first batch of particle generation to randomly generate 4,115 seeds, and finish generation when the solid-phase points grow to 469,000 required for the current batch. Generate the third batch of particles, namely the last batch of particles. In case of the particle radius of 1, randomly generate 34,840 seeds, and finish generation of the particles when solid-phase points grow to 174,200 which reach the total number for the batch, and the total number of particles reaches the total number of solid-phase points needed by the system.

Figure 3:
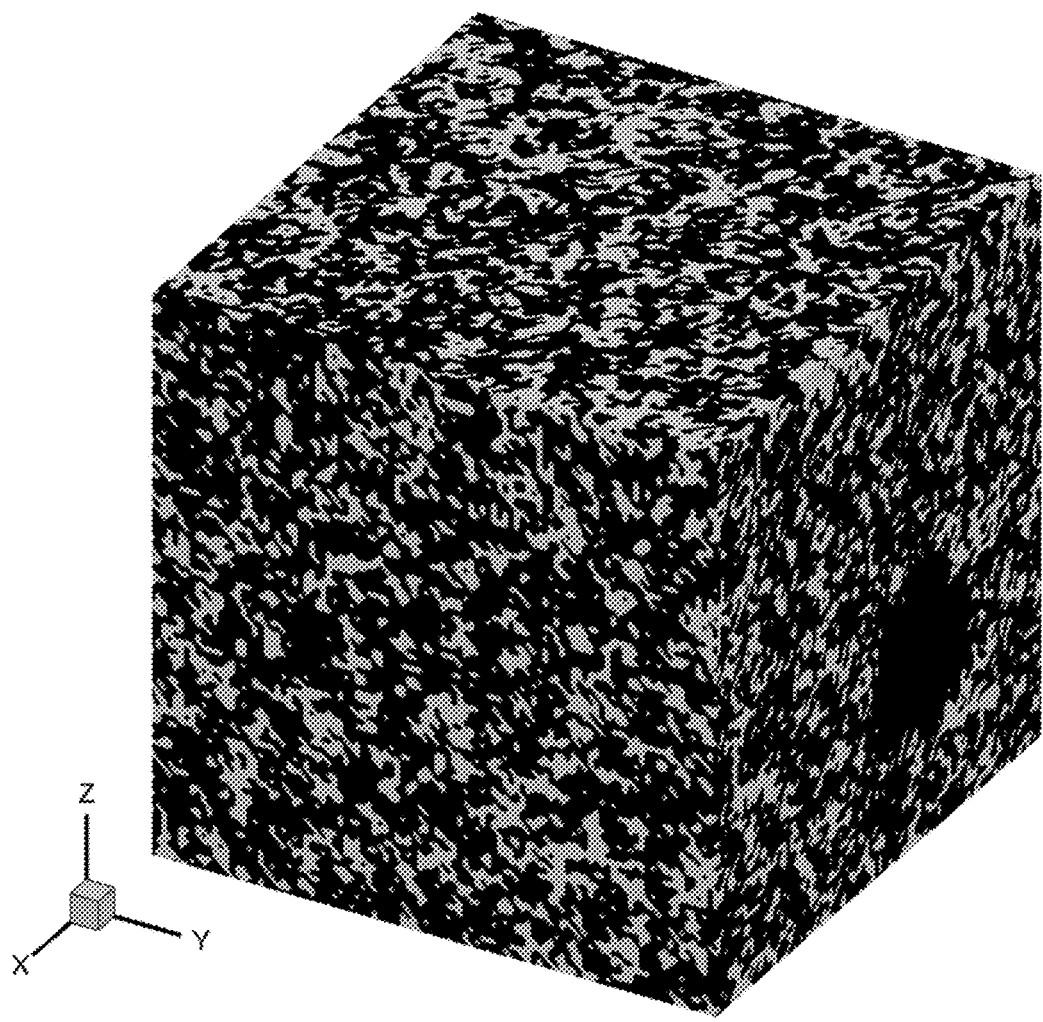
FIG. 3 is a visualized oblique view according to an embodiment of the present disclosure.
Figure 4:
FIG. 4 is a visualized cross-sectional view according to an embodiment of the present disclosure.

The results show that a data file is generated, which can be opened by post-processing software to view the generated structure in a form of porous media. For example, FIG. 3 is a 3D view, and FIG. 4 is a cross-sectional view of a grid at the 50th layer in the x direction.

Results prove that the simulation target in this embodiment is the soil structure of clayey silty sand in a hydrate reservoir of Shenhu Area located in the South China Sea. The geological conditions are different from those of normal hydrate reservoirs, with small particles leading to small porosity and lower permeability. The permeability of a sandstone structure in a common hydrate reservoir can reach about 1D (Li J F, Ye J L, Qin X W, et al. The first offshore natural gas hydrate production test in South China Sea[J]. China Geology, 2018, 1 (1):5-16.), whilst the experimental calculated value of permeability of a clayey silt structure in Shenhu area is only 2-200 mD (Bian H, Xia Y, Lu C, et al. Pore Structure Fractal Characterization and Permeability Simulation of Natural Gas Hydrate Reservoir Based on CT Images[J]. Geofluids, 2020, 2020:1-9.) (Li J F, Ye J L, Qin X W, et al. The first offshore natural gas hydrate production test in South China Sea[J]. China Geology, 2018, 1 (1):5-16.).

Regarding the model constructed according to the embodiment of the present disclosure, the permeability of porous media is calculated by Lattice Boltzmann Method (LBM), and the simulated result is 72.8 mD, which is within a reasonable range. Therefore, the structural model in accordance with the geological characteristics can be obtained by using the method.

What is claimed is:

1. A random particle generation method based on particle size distribution, comprising:
   step 1, obtaining geological structure-related information, and determining a simulation target, wherein the geological structure-related information comprises particle size distribution-related information and porosity of target soil;
   step 2, determining initial parameters of a simulation system, comprising a size of a three-dimensional region of the simulation system, porosity of a simulation system, particle size distribution-related information of the simulation system, and a growth probability of a solid-phase point of the simulation system in each direction; wherein the porosity of the simulation system refers to the porosity of the target soil in step 1, and the particle size distribution-related information of the simulation system refers to the particle size distribution-related information of the target soil, and is indicative of a correspondence between a particle size and a distribution probability of a particle;
   step 3, determining, according to the initial parameters in step 2, an estimated value in a simulation process, wherein step 3 specifically comprises:
   step 3.1, setting: total number of solid-phase points of the simulation system=total number of grids in a simulation region×(1−porosity);
   step 3.2, setting: total number N of solid-phase points of particles with a same particle size=distribution probability corresponding to each particle size×total number of grids in the system;
   step 3.3, setting: upper bound of solid-phase points of an individual particle n=nD$^3$/6, wherein D denotes a particle diameter; and
   step 3.4, setting: number of random seeds with a particle size of D=total number of particles with a particle size of D=N/n), wherein N/n is rounded up to an integer;
   step 4, constructing porous media by generating particles in batches in a descending order of particle sizes, wherein step 4 specifically comprises:
   step 4.1, constructing a first batch of particles with a particular particle size: generating and numbering seeds of N/n particles, and growing subsequent particles based on the seeds, wherein the growth of the particle matches the growth probability of the solid-phase point in each direction in step 2, and the generated solid-phase point is numbered in the same way as the seed; by traversing the solid-phase point for growth, determining whether the particle grows to the upper bound n of solid-phase points for an individual particle, and if so, stopping growth of the particle; and if the total number N of solid-phase points of the particle with the particle size is reached in the traversal process, finishing constructing the batch of particles with the particle size;

step 4.2, generating a subsequent batch of particles: after the previous batch of particles are generated, calculating a minimum distance I of each of pore points from the solid-phase point, randomly generating a latter batch of seeds on the pore points meeting the condition I≥½D, and then carrying out the same construction step as step 4.1 until the number of solid-phased points required for the batch of particles is reached, wherein D represents a particle size of the present batch of particles; and step 4.3, repeating step 4.2 to generate subsequent particles, and when a last batch of particles with a particular particle size are generated, determining whether the total number of solid-phase points in the system reaches the total number of solid-phase points in the simulation system in step 3.1, and if so, finishing the generation step;

step 5, restoring a soil structure according to the porous media; and step 6, conducting fossil energy exploitation according to the soil structure.

2. The random particle generation method based on particle size distribution according to claim 1, wherein in step 1, the particle size distribution-related information of the target soil is determined by dividing the range of a particle size into n segments with each segment containing multiple data points, taking a weighted average of the particle sizes of the data points with respect to the distribution probability within each segment of range as a particle size of the segment, and taking a sum of the distribution probability of the data points within each segment of range as a distribution probability of the segment.

3. The random particle generation method based on particle size distribution according to claim 2, wherein in step 1, n is ranging from 2 to 7.

4. The random particle generation method based on particle size distribution according to claim 1, wherein the growth probability of the solid-phase point of the simulation system in each direction as determined in step 2 refers to the probability that a central solid-phase point achieves solid-phase growth in each direction; and there are 26 growth directions for the solid-phase point, comprising 6 face-centered directions, 12 edge-centered directions and 8 corner-point directions, totally three major directions.

5. The random particle generation method based on particle size distribution according to claim 4, wherein in step 2, if the particles have isotropic structures, a growth probability in each of the major directions is the same.

6. The random particle generation method based on particle size distribution according to claim 5, wherein in step 2, a growth probability P1 in each of the 6 face-centered directions is 0.001-0.0001, a growth probability P2 in each of the 12 edge-centered directions meets $P2=P\frac{1}{4}$, and a growth probability P3 in each of the 8 corner-point directions meets $P3=P\frac{1}{16}$.

7. The random particle generation method based on particle size distribution according to claim 1, wherein in step 2, the three-dimensional region of the simulation system is a square structure.

8. The random particle generation method based on particle size distribution according to claim 1, wherein in step 2, the three-dimensional region of the simulation system is a square grid structure with a size of 100*100*100.

* * * * *